United States Patent [19]

Stack et al.

[11] Patent Number: 6,037,447
[45] Date of Patent: Mar. 14, 2000

[54] GLYCOPEPTIDE COMPOUNDS

[75] Inventors: Douglas R Stack, Fishers; Richard C Thompson, Frankfort, both of Ind.

[73] Assignee: Eli Lilly and Company, Indianapolis, Ind.

[21] Appl. No.: 09/125,496

[22] PCT Filed: Apr. 7, 1997

[86] PCT No.: PCT/US97/05735

§ 371 Date: Aug. 31, 1998

§ 102(e) Date: Aug. 31, 1998

[87] PCT Pub. No.: WO97/38706

PCT Pub. Date: Oct. 23, 1997

Related U.S. Application Data

[60] Provisional application No. 60/015,300, Apr. 12, 1996, and provisional application No. 60/031,735, Nov. 25, 1996.

[51] Int. Cl.$^7$ ..................................................... A61K 38/14
[52] U.S. Cl. ........................ 530/322; 530/317; 530/345; 514/8; 514/9
[58] Field of Search ..................................... 530/317, 322, 530/345; 514/8, 9

[56] References Cited

U.S. PATENT DOCUMENTS 4,521,335  6/1985  Chan et al. ........................... 260/112.5

OTHER PUBLICATIONS

Linsdell, H., et al., *J. Antibiotics*, vol. 49, No. 2, 181–193.
Sundram, U.N., et al., *J. Am. Chem. Soc.*, vol. 118, No. 51, 13107–13108 (1996).
Gerhard, J. Am. Chem. Soc. 115, 232, 1993.

*Primary Examiner*—Michael P. Woodward
*Assistant Examiner*—David Lukton
*Attorney, Agent, or Firm*—Arlene K. Musser

[57] ABSTRACT

The present invention is directed to certain glycopeptide dimers in which two glycopeptide units are covalently linked to one another through their disaccharide amine, via a linking radical. This invention is also directed to the monomeric intermediates. All of these compounds are useful as antibacterials, especially for the control of gram positive bacteria; the compounds are particularly useful for the control of resistant bacterial strains, such as vancomycin-resistant-enterococci ("VRE").

15 Claims, No Drawings

GLYCOPEPTIDE COMPOUNDS

This application claims priority from provisional application Ser. No. 60/015,300, filed Apr. 12, 1996, and provisional application Ser. No. 60/031,735, filed Nov. 25, 1996.

The present invention is directed to certain glycopeptide dimers in which two glycopeptide units are covalently linked to one another through their disaccharide amine, via a linking radical. This invention is also directed to the monomeric intermediates. All of these compounds are useful as antibacterials, especially for the control of gram positive bacteria; the compounds are particularly useful for the control of resistant bacterial strains, such as vancomycin-resistant-enterococci ("VRE").

The compounds of the present invention are defined by the following Formulae I and II:

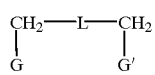  I

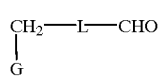  II

In the above formulae, each of G and G' is independently selected from the group consisting of deshydrovancomycin of the formula:

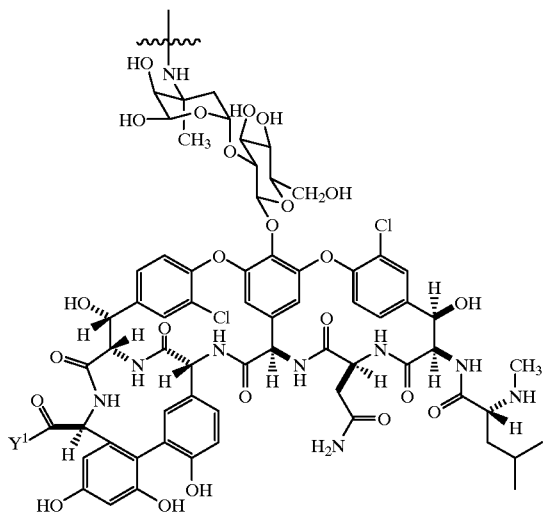

and deshydroA82846B of the formula:

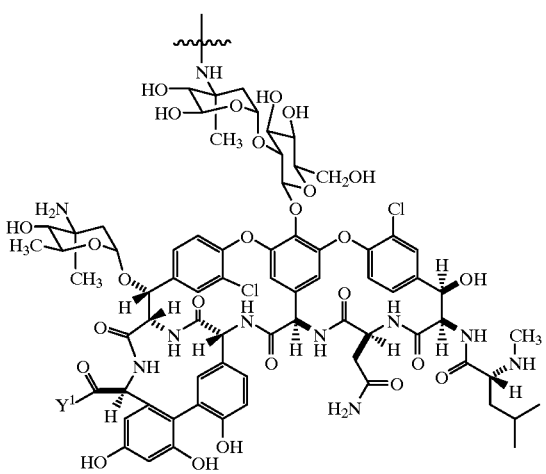

wherein $Y^1$ is OH or

and $Y^2$ is defined as follows:
(1) each $Y^2$ independently represents
hydrogen,
alkyl of $C_1$–$C_{10}$,
cycloalkyl of $C_5$–$C_6$,
cycloalkenyl of $C_5$–$C_6$,
naphthyl,
biphenylyl,
radical of the formula -$Y^3$-$(Y^4)_{0, 1, or 2}$, wherein $Y^3$ is loweralkyl of $C_1$–$C_6$ optionally substituted by from one to three substituents, each of which is independently selected from the group consisting of halo, nitro, cyano, alkoxy, haloalkyl, and haloalkoxy; and $Y^4$ is

wherein each $Y^5$ is independently hydrogen or loweralkyl of $C_1$–$C_4$, or $Y^4$ is phenyl or phenyl substituted with from one to three substituents, each of which is independently
halo,
nitro,
loweralkyl of $C_1$–$C_4$, cycloalkyl of $C_5$–$C_6$,
loweralkoxy of $C_1$–$C_4$,
haloloweralkyl of $C_1$–$C_4$, or
haloloweralkoxy of $C_1$–$C_4$; or (2) one $Y^2$ is hydrogen and the other $Y^2$ is (2-furanon-3-yl); or (3) both $Y^2$s are taken together with the nitrogen and constitute a five- to seven-membered heterocyclic ring optionally containing in addition to the indicated nitrogen atom one additional hetero ring atom which is nitrogen, oxygen, or sulfur, and which heterocyclic radical can be unsubstituted or substituted with from one or two substituents, each of which is loweralkyl of $C_1$–$C_2$, loweralkoxy of $C_1$–$C_2$, phenyl, benzyl, or $C_1$–$C_6$-alkanoyl;

and L is a divalent linking radical of the formula A:

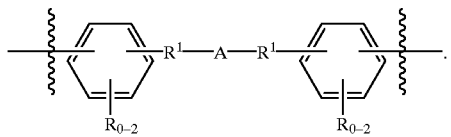

wherein A is:
  alkylene of $C_1$–$C_{16}$,
  (alkylene of $C_1$–$C_4$—X')$_q$-alkylene of $C_1$–$C_4$, wherein q is 1–3,

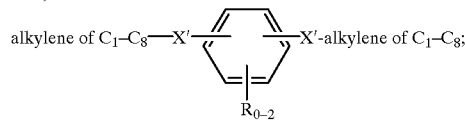

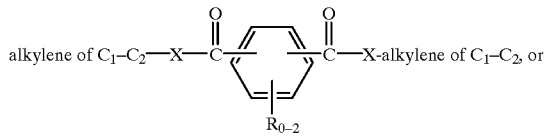

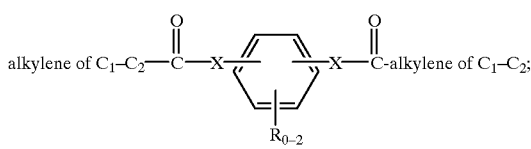

each $R^1$ is independently
  $CH_2$,
  O,
  S,
  ,
  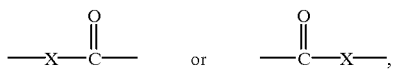
  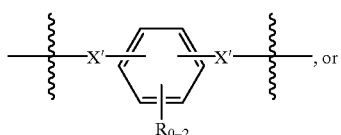
  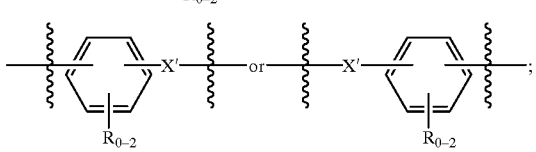

wherein each R independently represents halo, loweralkyl of $C_1$–$C_6$, loweralkoxy of $C_1$–$C_6$, phenyl, or phenyl substituted by from 1 to 2 substituents, each of which is independently halo, loweralkyl of $C_1$–$C_6$, or loweralkoxy of $C_1$–$C_6$; each X is independently —O— or

wherein $R^2$ is H or loweralkyl of $C_1$–$C_4$; and each X' is independently —O—, —S—, or

wherein $R^2$ is as defined above; or L is a divalent linking radical of the formula B:

B. -alkylene of $C_1$–$C_8$—$R^3$—X"-$R^3$-alkylene of $C_1$–$C_8$— wherein X" represents alkylene of $C_1$–$C_4$ or a phenylene of the formula

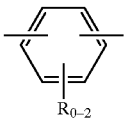

wherein R is as defined above; and each $R^3$ is independently $CH_2$ or O.

The present invention also includes salts of the foregoing compounds.

DETAILED DESCRIPTION OF THE INVENTION

In compounds of Formula I, the glycopeptide units, G and G', may be identical or different. In compounds of both Formulae, linkage of the glycopeptide units is through the amine group of the disaccharide sugar. Any "alkylene" of $C_2$ or higher can be straight chain or branched.

Certain compounds of the present invention are preferred. Compounds of Formula I, and especially symmetrical compounds (G=G' and/or both $R^1$ are identical), are preferred for their more efficient synthesis.

Antibacterial activity is enhanced by employing preferred "L" groups. Preferences include the following, individually and in any combination:
  L=a linking radical of formula A
  L=a linking radical of formula B wherein the carbon attached to —$CH_2$—G or to —$CH_2$—G' is branched
  $R^1$=O
  A=alkylene of $C_1$–$C_{16}$, especially straight-chain and especially $C_6$–$C_{12}$;
  A=(alkylene of $C_1$–$C_4$—X')$_q$-alkylene of $C_1$–$C_4$, especially wherein X'=O; the alkylene is —$(CH_2)_2$—; and q=2;
  R=phenyl and substituted phenyl, especially chlorophenyl; and especially when R has this value on a phenyl ring within "A".

Other preferences will be apparent from the further teachings herein.

Representative compounds of the present invention are set forth in following TABLES 1 and 2. TABLE 1 identifies dimers of Formula I; TABLE 2 identifies compounds of Formula II.

TABLE 1

| Ex. # | G | G' | L | Name |
|---|---|---|---|---|
| 1 | Vanco | Vanco | —O—(CH₂)₂—O— (with 1,4-phenylene linkers on both sides) | 1,2-ethanediyl-bis-[(oxy-4,1-phenylene)methylene]-bis-[vancomycin] |
| 2 | Vanco | Vanco | —O—(CH₂)₄—O— (with phenylene linkers) | 1,4-butanediyl-bis-[(oxy-2,1-phenylene)-methylene]-bis-[vancomycin] |
| 3 | Vanco | Vanco | —O—(CH₂)₅—O— (with 1,4-phenylene linkers) | 1,5-pentanediyl-bis-[(oxy-4,1-phenylene)-methylene]-bis-[vancomycin] |
| 4 | Vanco | Vanco | —O—(CH₂)₅—O— (with 1,3-phenylene linkers) | 1,5-pentanediyl-bis-[(oxy-3,1-phenylene)-methylene]-bis-[vancomycin] |
| 5 | Vanco | Vanco | —O—(CH₂)₆—O— (with 1,4-phenylene linkers) | 1,6-hexanediyl-bis-[oxy-4,1-phenylene]-bis-methylene]-bis-[vancomycin] |
| 6 | Vanco | Vanco | —O—(CH₂)₂—CH(CH₃)—(CH₂)₂—O— (with 1,4-phenylene linkers) | [3-methyl-1,5-pentanediyl-bis[(oxy-4,1-phenylene)-methylene]-bis-[vancomycin] |
| 7 | Vanco | Vanco | —O—(CH₂)₇—O— (with 1,4-phenylene linkers) | 1,7-heptanediyl-bis-[oxy-4,1-phenylene)-methylene]-bis-[vancomycin] |

TABLE 1-continued

| Ex. # | G | G' | L | Name |
|---|---|---|---|---|
| 8 | Vanco | Vanco | —⟨C₆H₄⟩—O—(CH₂)₈—O—⟨C₆H₄⟩— | 1,8-octanediyl-bis-[(oxy-4,1-phenylene)-methylene]-bis-[vancomycin] |
| 9 | Vanco | Vanco | —⟨C₆H₄⟩—O—(CH₂)₉—O—⟨C₆H₄⟩— | 1,9-nonanediyl-bis-[(oxy-4,1-phenylene)-methylene]-bis-[vancomycin] |
| 10 | Vanco | Vanco | —⟨C₆H₄⟩—O—(CH₂)₂—O—(CH₂)₂—O—⟨C₆H₄⟩— | 1,2-ethanediyl-bis-[oxy-1,2-ethyleneoxy-4,1-phenylene]-bis-[vancomycin] |
| 11 | Vanco | Vanco | —C(=O)O(CH₂)₂—O—⟨C₆H₄⟩—C(=O)O(CH₂)₂— | 1,4-phenylene-bis-[(carbonyloxy-1,2-ethylene-oxy-2,1-phenylene)]-methylene]-bis-[vancomycin] |
| 12 | Vanco | Vanco | —⟨C₆H₄⟩—O—(CH₂)₃—⟨C₆H₄⟩—(CH₂)₃—O—⟨C₆H₄⟩— | 1,3-phenylene-bis-[(oxy-1,3-n-propyleneoxy-4,1-phenylene)]-methylene]-bis-[vancomycin] |
| 13 | A82846B | Vanco | —⟨C₆H₄⟩—O—(CH₂)₈—O—⟨C₆H₄⟩— | 1,8-octanediyl-bis-[(oxy-4,1-phenylene)-methylene]-[vancomycin][A82846B] |
| 14 | A82846B | A82846B | —⟨C₆H₄⟩—O—(CH₂)₃—O—⟨C₆H₄⟩— | 1,3-propanediyl-bis-[(oxy-4,1-phenylene)-methylene]-bis-[A82846B] |

TABLE 1-continued

| Ex. # | G | G' | L | Name |
|---|---|---|---|---|
| 15 | A82846B | A82846B | —O—(CH₂)₄—O— with two phenyl groups | 1,4-butanediyl-bis-[(oxy-2,1-phenylene)-methylene]-bis-[A82846B] |
| 16 | A82846B | A82846B | —O—(CH₂)₅—O— with two 1,4-phenylene groups | 1,5-pentanediyl-bis-[(oxy-4,1-phenylene)-methylene]-bis-[A82846B] |
| 17 | A82846B | A82846B | —O—(CH₂)₅—O— with 1,3-phenylene groups | 1,5-pentanediyl-bis-[(oxy-3,1-phenylene)-methylene]-bis-[A82846B] |
| 18 | A82846B | A82846B | —O—(CH₂)₆—O— with two 1,4-phenylene groups | 1,6-hexanediyl-bis-[(oxy-4,1-phenylene)-methylene]-bis-[A82846B] |
| 19 | A82846B | A82846B | —O—(CH₂)₂—CH(CH₃)—(CH₂)₂—O— with two 1,4-phenylene groups | [3-methyl-1,5-pentanediyl]-bis[(oxy-4,1-phenylene)-methylene]-bis-[A82846B] |
| 20 | A82846B | A82846B | —O—(CH₂)₇—O— with two 1,4-phenylene groups | 1,7-heptanediyl-bis-[(oxy-4,1-phenylene)-methylene]-bis-[A82846B] |
| 21 | A82846B | A82846B | —O—(CH₂)₈—O— with two 1,4-phenylene groups | 1,8-octanediyl-bis-[(oxy-4,1-phenylene)-methylene-bis[A82846B] |
| 22 | A82846B | A82846B | —O—(CH₂)₈—O— with two 1,4-phenylene groups | 1,8-octanediyl-bis-[(oxy-4,1-phenylene)-methylene-bis[A82846B]·HCl salt |

TABLE 1-continued

.HCl salt

| Ex. # | G | G' | L | Name |
|---|---|---|---|---|
| 23 | A82846B | A82846B | phenyl—O—(CH₂)₈—O—phenyl | 1,8-octanediyl-bis-[(oxy-3,1-phenylene)-methylene]-bis-[A82846B] |
| 24 | A82846B | A82846B | (n-pentyl substituted phenyl)—O—(CH₂)₈—O—(n-pentyl substituted phenyl) | 1,8-octanediyl-bis-[(oxy-3-n-pentyloxy-4,1-phenylene)methylene]-bis[A82846B] |
| 25 | A82846B | A82846B | phenyl—O—(CH₂)₉—O—phenyl | 1,9-nonanediyl-bis-[(oxy-4,1-phenylene)-methylene]-bis-[A82846B] |
| 26 | A82846B | A82846B | phenyl—O—(CH₂)₁₀—O—phenyl | 1,10-decanediyl-bis-[(oxy-4,1-phenylene)-methylene]-bis-[A82846B] |
| 27 | A82846B | A82846B | phenyl—O—(CH₂)₁₂—O—phenyl | 1,12-dodecanediyl-bis-[(oxy-4,1-phenylene)-methylene]-bis-[A82846B] |
| 28 | A82846B | A82846B | phenyl—O—(CH₂)₁₆—O—phenyl | 1,16-hexadecanediyl-bis-[(oxy-4,1-phenylene)-methylene]-bis-[A82846B] |
| 29 | A82846B | A82846B | phenyl—O—(CH₂)₂—O—(CH₂)₂—O—(CH₂)₂—O—phenyl | 1,2-ethanediyl-bis-[(oxy-1,2-ethyleneoxy-4,1-phenylene)methylene]-bis[A82846B]] |

TABLE 1-continued

| Ex. # | G | G' | L | Name |
|---|---|---|---|---|
| 30 | A82846B | A82846B | | 1,3-phenylene-bis-[(oxy-1,3-n-propyleneoxy-4,1-phenylene)methylene]-bis[A82846B] |
| 31 | A82846B | A82846B | | 1,4-phenylene-bis-[(carbonyloxy-1,2-ethyleneoxy-2,1-phenylene)methylene]-bis[A82846B] |
| 32 | A82846B | A82846B | | 1,3-[5-biphenylyl-bis-[(oxy-1,3-n-propyleneoxy-4,1-phenylene)methylene]-bis[A82846B] |
| 49 | A82846B | A82846B | | 1,6-hexanediylbis[oxy-[4,4'-biphenylene]-methylene]bis(A82846B) |
| 50 | A82846B | A82846B | | 1,3-phenylenebis[oxy-1,5-n-pentyleneoxy[4,1-phenylene]methylene]-bis(A82846B) |
| 51 | A82846B | A82846B | | 1,8-octanediylbis[oxy-4-phenyl-[3,1-phenylene]-methylene]bis(A82846B) |

TABLE 1-continued

| Ex. # | G | G' | L | Name |
|---|---|---|---|---|
| 53 | Vanco | Vanco | [phenyl-O-(CH2)8-O-phenyl] | 1,8-octanediylbis-[oxy-[3,1-phenylene]-methylene]-bis[vancomycin] |
| 54 | Vanco | Vanco | [biphenyl-O-(CH2)6-O-biphenyl] | 1,6-hexanediylbis[oxy-[4,4'-biphenylene]-methylene]-bis[vancomycin] |
| 55 | Vanco | Vanco | [iodophenyl-O-(CH2)8-O-iodophenyl] | 1,8-octanediylbis-[(oxy-4-iodo-3,1-phenylene)methylene]bis[vancomycin] |
| 56 | Vanco | Vanco | [phenyl-biphenyl-O-(CH2)8-O-biphenyl-phenyl] | 1,8-octanediylbis-[oxy-[4-phenyl-3,1-phenylene]-methylene]bis[vancomycin] |
| 57 | Vanco | Vanco | [C(CH3)2-phenyl-O-(CH2)4-O-phenyl-C(CH3)2] | 1,3-phenylene-bis-[oxy-[5-methyl-5,1-hexylene]-bis[vancomycin] |
| 58 | Vanco | Vanco | [C(CH3)2-(CH2)4-O-(CH2)4-O-(CH2)4-C(CH3)2] | 1,4-butanediylbis-[oxy-[5-methyl-5,1-hexylene]-bis[vancomycin] |

TABLE 1-continued

| Ex. # | G | G' | L | Name |
|---|---|---|---|---|
| 59 | Vanco | Vanco | 4,1-phenylene–O–(CH₂)₁₂–O–4,1-phenylene | 1,12-dodecanediyl-bis-[(oxy-4,1-phenylene)-methylene]-bis[vancomycin] |
| 60 | Vanco | Vanco | 4,1-phenylene–O–(CH₂)₃–O–1,3-phenylene–O–(CH₂)₃–O–4,1-phenylene | 1,3-phenylene-bis-[(oxy-1,3-n-propyleneoxy-4,1-phenylene]methylene]-bis[vancomycin].3HCl salt |
| 61 | Vanco | Vanco | 4,1-phenylene–O–(CH₂)₃–O–(5-n-C₅H₁₁-1,3-phenylene)–O–(CH₂)₃–O–4,1-phenylene | 5-n-pentyl-1,3-phenylene-bis[(oxy-1,3-n-propyleneoxy-4,1-phenylene)methylene]-bis[vancomycin] |
| 62 | A82846B | A82846B | 4,1-phenylene–O–(CH₂)₈–O–(4-iodo-3,1-phenylene) | 1,8-octanediylbis-[(oxy-4-iodo-3,1-phenylene)methylene]-bis[A82846B] |
| 63 | A82846B | A82846B | 4,1-phenylene–O–(CH₂)₄–C(CH₃)₂–C(CH₃)₂–(CH₂)₄–O–1,3-phenylene | 1,3-phenylene-bis-[oxy-5-methyl-[A82846B] |
| 64 | A82846B | A82846B | 4,1-phenylene–O–(CH₂)₇–O–1,3-phenylene–O–(CH₂)₇–O–4,1-phenylene | 1,3-phenylene-bis-[(oxy-1,7-n-heptyleneoxy-4,1-phenylene)methylene]-bis[A82846B] |

TABLE 1-continued

| Ex. # | G | G' | L | Name |
|---|---|---|---|---|
| 65 | A82846B | A82846B | ~~~(CH₂)₄—O—(CH₂)₄—C(CH₃)₂—(CH₂)₄—O—(CH₂)₄~~~ | 1,4-butanediylbis[oxy-5-methyl-5,1-hexylene]-bis-[A82846B] |
| 66 | A82846B | A82846B | ~~~-C₆H₄-O-(CH₂)₃-O-C₆H₄-~~~ | 1,3-phenylene-bis[(oxy-1,3-n-propyleneoxy-4,1-phenylene)methylene]-bis[A82846B] |
| 70 | A82846B, (3-dimethyl amino propyl)-amide | A82846B | ~~~-C₆H₄-O-(CH₂)₃-O-C₆H₄-~~~ | 1,3-phenylenebis[oxy-1,3-n-propylene-oxy-4,1-phenylene]methylene] A82846B/A82846B,(3-dimethylaminopropyl)amide |
| 71 | A82846B, (3-dimethyl amino propyl)-amide | A82846B, (3-dimethyl amino propyl)-amide | ~~~-C₆H₄-O-(CH₂)₃-O-C₆H₄-~~~ | 1,3-phenylenebis[oxy-1,3-n-propylene-oxy-4,1-phenylene)methylene]bis-[A82846B,(3-dimethylaminopropyl)-amide] |

TABLE 2

| Ex. # | G | L | Name |
|---|---|---|---|
| 33 | Vanco | —C₆H₄—O—(CH₂)₂—O—C₆H₄— | $N^4$-(4-(2-(p-formylphenoxy)-ethoxy)benzyl)vancomycin |
| 34 | Vanco | —C₆H₄—O—(CH₂)₃—O—C₆H₄— | $N^4$-(4-(3-(p-formylphenoxy)-n-propyloxy)benzyl)vancomycin |
| 35 | Vanco | —C₆H₄—O—(CH₂)₄—O—C₆H₄— | $N^4$-(4-(4-(p-formylphenoxy)-n-butoxy)benzyl)vancomycin |
| 36 | Vanco | —C₆H₄—O—(CH₂)₅—O—C₆H₄— | $N^4$-(4-(5-(p-formylphenoxy)-n-pentyloxy)benzyl)vancomycin |
| 37 | Vanco | —C₆H₄—O—(CH₂)₆—O—C₆H₄— | $N^4$-(4-(6-(p-formylphenoxy)-n-hexyloxy)benzyl)vancomycin |
| 38 | Vanco | —C₆H₄—O—(CH₂)₂—CH(CH₃)—(CH₂)₂—O—C₆H₄— | $N^4$-(4-(5-(p-formylphenoxy)-3-methyl-n-pentyloxy)benzyl)-vancomycin |
| 39 | Vanco | —C₆H₄—O—(CH₂)₇—O—C₆H₄— | $N^4$-(4-(7-(p-formylphenoxy)-n-heptyloxy)benzyl)vancomycin |
| 40 | Vanco | —C₆H₄—O—(CH₂)₈—O—C₆H₄— | $N^4$-(4-(8-(p-formylphenoxy)-n-octyloxy)benzyl)vancomycin |

TABLE 2-continued

| Ex. # | G | L | Name |
|---|---|---|---|
| 41 | Vanco |  | $N^4$-(4-(10-(p-formylphenoxy)-n-decyloxy)benzyl)vancomycin |
| 42 | Vanco |  | $N^4$-(4-(12-(p-formylphenoxy)-n-dodecyloxy)benzyl)vancomycin |
| 43 | Vanco | 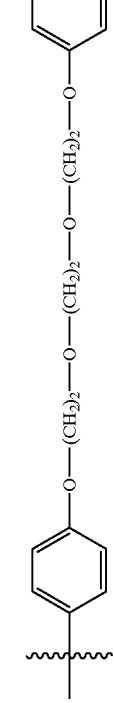 | $N^4$-(4-(2-(2-(2-(p-formylphenoxy)ethoxy)ethoxy)benzyl)A82846B |
| 44 | Vanco | 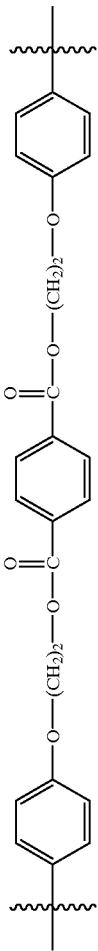 | $N^4$-(4-(2-(4-(2-(p-formylphenoxy)ethoxycarbonyl)benzoyloxy)ethoxy)benzyl)vancomycin |
| 45 | Vanco | 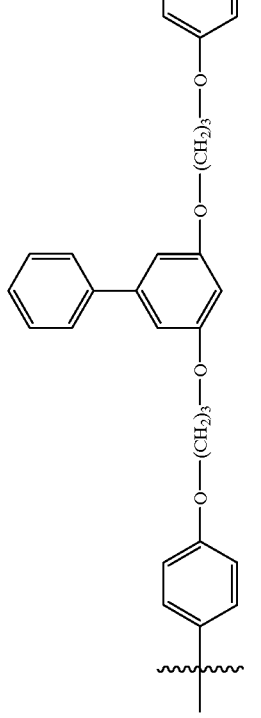 | $N^4$-(4-(3-(3-(p-formylphenoxy)-n-propoxy)-5-phenylphenoxy)-n-propoxy)benzyl)vancomycin |
| 46 | A82846B | 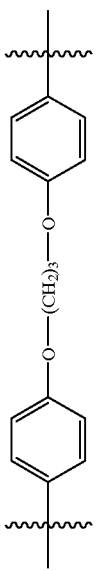 | $N^4$-(4-(3-(p-formylphenoxy)-n-propyloxy)benzyl)A82846B |
| 47 | A82846B | 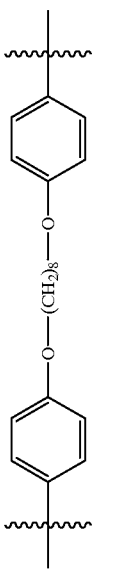 | $N^4$-(4-(8-(p-formylphenoxy)-n-octyloxy)benzyl)A82846B |

TABLE 2-continued

| Ex. # | G | L | Name |
|---|---|---|---|
| 48 | A82846B |  | $N^4$-(4-(12-(p-formylphenoxy)-n-dodecyloxy)benzyl)A82846B |
| 52 | Vanco | 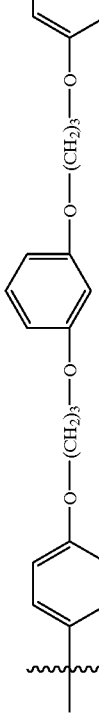 | $N^4$-(4(3-(3-(p-formylphenoxy)-n-propyloxy)phenoxy)-n-propyloxy)-benzyl)vancomycin |
| 67 | Vanco | 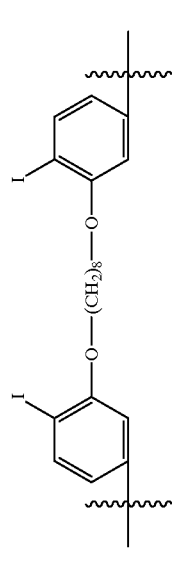 | $N^4$-(3-(8-(5-formyl-2-iodophenoxy)-n-octyloxy)-4-iodobenzyl)-vancomycin |
| 68 | Vanco | 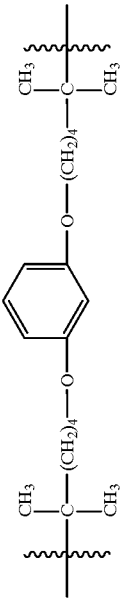 | $N^4$-(6-(3-(5-formyl-5-methyl-n-hexyloxy)phenoxy)-2,2-dimethylhexyl)vancomycin |
| 69 | Vanco | 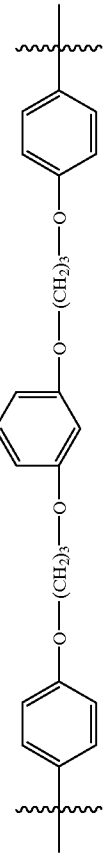 | $N^4$-(4-(3-(3-(p-formylphenoxy)-n-propyloxy)-5-n-pentyloxy)-benzyl)-vancomycin |

The compounds of the present invention are prepared by reacting vancomycin or A82846B with a bisaldehyde of the formula:

 III to form an intermediate Schiff base, which is subsequently reduced to obtain the compounds of Formula I and II.

Many of the bisaldehydes to be employed as starting materials are known compounds. All of them can be prepared by techniques known to those skilled in the art, per various references;

*J. Ora. Chem.,* 26, 474, (1961)

*J. Het. Chem.,* 27, 1007 (1990)

*J.A.C.S.,* 73, 1872 (1951)

*J.A.C.S.,* 109, 2260 (1987)

*J. Chem. Soc. Perkin I,* 189 (1983)

*Syn. Comm.,* 18(12), 1379 (1988)

*Chem. Letters,* 587 (1995)

*Macromolecules,* 6045 (1992);

*J. Chem. Soc. Chem. Comm.* 1463 (1991)

*J. Polym. Sci. Part A, Polymer Chem.* 31(12) 2899 (1993)

*J. Chem. Res. Synop.* (8), 296 (1994)

*Farmco Ed. Sci.* 15, 468 (1960)

*Makromol. Chem.* 191 (4) 815 (1990)

*J. Polym. Sci. Part A, Polymer Chem.* 29(3) 361 (1991)

*Makromol. Chem.* 65, 54 (1963)

The reaction of bisaldehyde with vancomycin or A82846B is carried out in accordance with prior art condensations of amine and aldehyde to form Schiff bases, and their subsequent reduction.

Thus, the present condensation is typically conducted in a polar solvent, such as dimethylformamide or methanol, or a mixture of polar solvents. The reaction goes forward over a range of temperatures, such as from 25° C. to 100° C., but is preferably conducted at temperatures of about 60° C. to 70° C. The reaction is preferably conducted under an inert atmosphere, such as nitrogen or argon.

The reaction yields a Schiff base of the formula

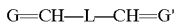

where both aldehyde groups have reacted with glycopeptide, or of the formula

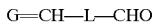

where only one aldehyde group has reacted with glycopeptide.

The Schiff base is subsequently reduced. Preferably, the reduction is conducted in the same reaction mixture in a polar solvent, and employing a chemical reducing agent. Metal borohydrides, such as sodium borohydride and sodium cyanoborohydride are preferred. The reaction goes forward over a range of temperatures, such as from about 25° C. to about 100° C.; preferably, the reaction is conducted at about 60° C. to 70° C.

Depending somewhat on concentration of reagents, the condensation of bisaldehyde with vancomycin or A82846B and subsequent reduction will yield a dimer of Formula I, a mono-substituted derivative of Formula II, or a mixture of both. Generally, both products are produced. However, some control of the products can be achieved by the amount of reactants employed. A dimer of Formula I requires two molecular proportions of vancomycin or A82846B per molecular proportion of bisaldehyde, whereas a compound of Formula II requires equimolar amounts of the reactants. Preferably the reaction is continued through the reduction, and the respective products separated at that time.

The product, or mixture of products, can be isolated and purified if desired in a conventional manner, such as by HPLC. Characterization of products is best accomplished by Fast Atom Bombardment Mass spectroscopy (FAB•MS).

In addition to the foregoing synthetic route, compounds of the present invention can be prepared in an alternate route. In this alternate route, a dimer is prepared by the foregoing synthetic route, and further changes to the structure of the glycopeptide are made subsequently. This approach to synthesizing the present dimers is illustrated by Preparations 7 and 8 below in which a dimer of the present invention is reacted with an amine to convert the acid of the glycopeptide to an amide

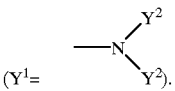

Other modifications of the glycopeptide portion of a dimer can likewise be made. Techniques for such modifications are known to those skilled in the art; see *Glycopeptide Antibiotics*, edited by Ramakrishnan Nagarajan (Marcel Dekker, Inc., New York, 1994), and references cited therein. This volume is incorporated herein by reference.

When it is desired to employ a salt, a compound of the present invention can be reacted with a mineral or organic acid or an inorganic base, in techniques well known to those skilled in the art. Pharmaceutically-acceptable salts are preferred.

The following examples report preparations of illustrative compounds of the present invention.

The HPLC procedures reported in these examples were as follows:

Analytical ("Conditions A"): Reactions were monitored by analytical HPLC using a Waters μBondapak $C_{18}$ column (3.9×300 mm) and UV detection at 280 nm. Elution was accomplished with a linear gradient of 5% $CH_3CN$—95% buffer to 80% $CH_3CN$—20% buffer over 30 minutes. The buffer used was 0.5% triethylamine in water, adjusted to pH 3 with $H_3PO_4$.

Preparative ("Conditions B"): Crude reaction mixtures were purified by preparative HPLC using a Waters $C_{18}$ Nova-Pak column (40×300 mm) and UV detection at 280 nm. Elution was accomplished with a linear gradient of 5% CH3CN—95% buffer to 80% $CH_3CN$—20% buffer over 30 minutes. The buffer used was 0.5% triethylamine in water, adjusted to pH 3 with $H_3PO_4$. The desired fractions were subsequently desalted with a Waters $C_{18}$ Sep-Pak (35 cc) followed by lyophilization. Alternatively, a buffer containing 0.1% TFA in $H_2O$ can be used, in which case the TFA salt is obtained directly after lyophilization.

Compounds were desalted as follows. A Waters Sep-Pak cartridge was pre-wet with methanol (2–3 column volumes) then conditioned with water (2–3 column volumes). The sample, dissolved in a minimum volume of water, was loaded onto the Sep-Pak column which was then washed with water (2–3 column volumes) to remove the unwanted salts. The product was then eluted with an appropriate solvent system, typically 1:1 $CH_3CN/H_2O$, $CH_3CN$, and/or methanol. The organic solvent component was removed in vacuo and the resulting aqueous solution lyophilized to give the final product.

Preparation 1

Synthesis of Example 5, 1,6-hexanediylbis[(oxy-4,1-phenylene)methylene]bis[vancomycin](One-pot Synthesis of Vancomycin Dimer)

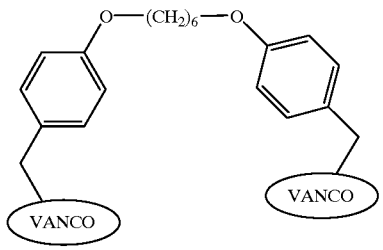

A dry 100 mL round bottom flask was charged with vancomycin.HCl (250 mg, 0.168 mmol.), and 1,6-bis(4'-formylphenoxy)-n-hexane (101 mg, 0.310 mmol.). Anhydrous DMF (6 mL) was added to the flask and the resulting mixture was stirred under $N_2$ and heated to 70° C. After 3.5 hours, sodium cyanoborohydride (80 mg, 1.3 mmol.) was added in one portion, and the reaction mixture was maintained at 70° C. for one additional hour. The reaction mixture was cooled, and stored at 0° C. overnight.

The reaction mixture was then concentrated in vacuo to give a residue which was re-dissolved in 1:1 $H_2O:CH_3CN$ (5 mL) and HOAc (0.5 mL). The resulting solution was purified by preparatory HPLC (conditions B). The desired fractions, as determined by analytical HPLC (conditions A), were concentrated in vacuo to ~1.5 mL, and desalted. After lyophilization, 1,6-hexanediylbis[(oxy-4,1-phenylene) methylene]bis[vancomycin] was obtained (24.3 mg, 0.008 mmol., 10.0% yield) as a white powder.

HPLC (conditions A) retention time: 13.6 min.

FABMS shows peak of (M+6H) at 3195.

Preparation 2

Synthesis of Example 25, 1,9-nonanediylbis[(oxy-4,1-phenylene)methylene]bis[A82846B](One-pot Synthesis of A82846 Dimer)

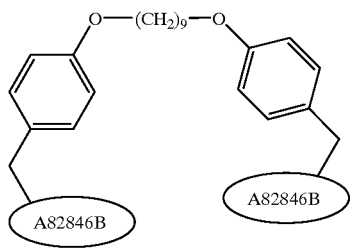

A dry 100 mL round bottom flask was charged with A82846B•tri-acetate salt (278 mg, 0.157 mmol.), and 1,9-bis-(4'-formylphenoxy)-n-nonane (103.7 mg, 0.282 mmol.). Anhydrous DMF (15 mL) and anhydrous MeOH (15 mL) were added to the flask and the resulting mixture was stirred under $N_2$ and heated to 70° C. After 3.5 hours, sodium cyanoborohydride (68 mg, 1.08 mmol.) was added in one portion, and the reaction mixture was maintained at 70° C. for one additional hour.

The reaction mixture was then concentrated in vacuo to give a residue which was re-dissolved in 1:1 $H_2O:CH_3CN$ (5 mL) and HOAc (0.5 mL). The resulting solution was purified by preparatory HPLC (conditions B). The desired fractions, as determined by analytical HPLC (conditions A), were concentrated in vacuo to ~1.5 mL, and desalted. After lyophilization, 1,9-nonanediylbis[(oxy-4,1-phenylene) methylene]bis[epivancomycin] was obtained (25.7 mg, 0.007 mmol., 9.3% yield) as a white powder.

HPLC (conditions A) retention time: 14.9 min.

FABMS shows peak of (M+5H) at 3522.

Preparation 3

Synthesis of Example 47, $N^4$-(4-(8-(p-formylphenoxy)-n-octyloxy)benzyl)A82846B (Synthesis of Formula II)

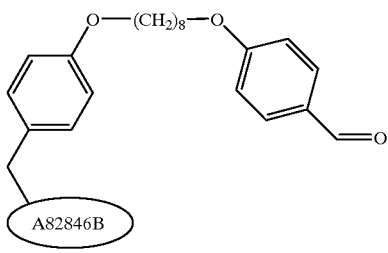

A dry 100 mL round bottom flask was charged with A82846B•tri-acetate salt (278 mg, 0.157 mmol.), and 1,8-bis-(4'-formylphenoxy)-n-octane (100 mg, 0.19mmol.). Anhydrous DMF (15 mL) and anhydrous MeOH (15 mL) were added to the flask and the resulting mixture was stirred under $N_2$ and heated to 70° C. After 3.5 hours, sodium cyanoborohydride (48 mg, 0.739mmol.) was added in one portion, and the reaction mixture was maintained at 70° C. for one additional hour.

The reaction mixture was then concentrated in vacuo to give a residue which was re-dissolved in 1:1 $H_2O:CH_3CN$ (5 mL) and HOAc (0.5 mL). The resulting solution was purified by preparatory HPLC (conditions B). The desired fractions, as determined by analytical HPLC (conditions A), were concentrated in vacuo to ~1.5 mL, and desalted. After lyophilization, $N^4$-(4-(8-(p-formylphenoxy)-n-octyloxy) benzyl)A82846B was obtained (26.3 mg, 0.013 mmol., 8.6% yield) as a white powder.

HPLC (conditions A) retention time: 19.9 min.

FABMS shows peak of (M+2H) at 1930.

Preparation 4

Synthesis of Example 13, 1,8-octanediylbis[(oxy-4,1-phenylene)methylene][vancomycin][A82846B] (Synthesis of Hybrid Dimer)

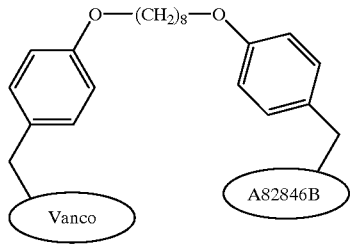

A dry round bottom flask was charged with vancomycin-.HCl (75 mg, 0.052 mmol.), and $N^4$-(4-(8-(p-formylphenoxy)-n-octyloxy)benzyl)A82846B (50 mg, 0.026 mmol.). Anhydrous DMF (6 mL) was added to the flask and the resulting mixture was stirred under $N_2$ and heated to 70° C. After 5 hours, sodium cyanoborohydride (59 mg, 0.93 mmol.) was added in one portion, and the reaction mixture was maintained at 70° C. for one additional hour. The reaction mixture was cooled, and stored at 0° C. overnight.

The reaction mixture was then concentrated in vacuo to give a residue which was re-dissolved in 1:1 $H_2O:CH_3CN$ (5 mL) and HOAc (0.5 ML). The resulting solution was purified by preparatory HPLC (conditions B). The desired fractions, as determined by analytical HPLC (conditions A), were concentrated in vacuo to ~1.5 mL, and desalted. After lyophilization, 1,8-octanediylbis[(oxy-4,1-phenylene) methylene][vancomycin][A82846B] was obtained (5.2 mg, 0.002 mmol., 7.6% yield) as a white powder.

HPLC (conditions A) retention time: 14.5 min.
FABMS shows peak of (M+6H) at 3364.

Preparations 5 & 6

Synthesis of Example 47, $N^4$-(4-(8-(p-formylphenoxy)-n-octyloxy)benzyl)A82846B, and Example 21, 1,8-octanediylbis[(oxy-4,1-phenylene)methylene]bis[A82846B](Two-step Synthesis of A82846 Dimer)

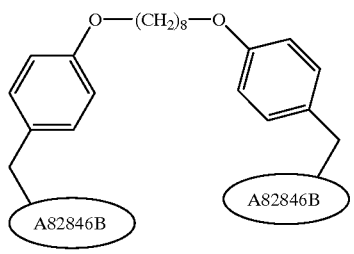

A dry flask was charged with A82846B•tri-acetate salt (5.0 g, 0.003 mol.), and 1,8-bis(4'-formylphenoxy)-n-octane (1.93 g, 0.006 mol.). Anhydrous DMF (300 mL) and anhydrous MeOH (300 mL) were added to the flask and the resulting mixture was stirred under $N_2$ and heated to 70° C. After 3.75 hours, sodium cyanoborohydride (0.76 g, 0.012 mol.) was added in one portion, and the reaction mixture was maintained at 70° C. for one additional hour. The reaction was cooled and stored at 0° C. overnight.

The reaction mixture was then concentrated in vacuo to give a residue which was re-dissolved in 1:1 $H_2O:CH_3CN$ (200 mL) and HOAc (5 mL). The resulting solution was purified by preparatory HPLC (conditions B). The desired fractions, as determined by analytical HPLC (conditions A), were concentrated in vacuo to ~1.5 mL, and desalted. After lyophilization, $N^4$-(4-(8-(p-formylphenoxy)-n-octyloxy) benzyl)A82846B was obtained (387.4 mg, 0.2 mmol., 6.6% yield) as a white powder.

HPLC (conditions A) retention time: 19.9 min.
FABMS shows peak of (M+3H)at 1932.

A dry flask was charged with $N^4$-(4-(8-(p-formylphenoxy)-n-octyloxy)benzyl)A82846B (20.0 mg, 0.01 mmol), and A82846B (32.9 mg, 0.021 mmol). Anhydrous DMF (3 mL) and anhydrous MeOH (3 mL) were added to the flask and the resulting mixture was stirred under $N_2$ and heated to 70° C. After 2 hours, sodium cyanoborohydride (5.0 mg, 0.079 mmol) was added in one portion, and the reaction mixture stirred an additional 0.25 hours.

The reaction mixture was then concentrated in vacuo to give a residue which was redissolved in 1:1 $H_2O:CH_3CN$ (5 mL). The resulting solution was purified by preparatory HPLC (conditions D). The desired fraction, as determined by analytical HPLC (conditions A), were concentrated in vacuo to ~1.5 mL, and desalted. After lyophilization, 1,8-octanediylbis[(oxy-4,1-phenylene)methylene]bis [A82846B] was obtained (3.0 mg, 0.001 mmol, 8.6% yield) as a white powder.

HPLC (conditions A) retention time: 13.6 min.
FABMS shows peak of (M+5H) at 3508.

Preparations 7 & 8

Synthesis of Example 70, 1,3-phenylenebis[oxy-1, 3-n-propylene-oxy-4,1-phenylene)methylene] A82846B/A82846B, (3-dimethylaminopropyl) amide, and Example 71, 1,3-phenylenebis[oxy-1,3-n-propylene-oxy-4,1-phenylene)methylene]bis [A82846B, (3-dimethylaminopropyl)amide]

A dry round bottom flask was charged with 1,3-phenylene-bis-[(oxy-1,3-n-propyleneoxy-4,1-phenylene) methylene]—bis[A82846B] (50.0 mg, 0.014 mmol) and 1 mL DMSO. PyBOP (14.5 mg, 0.028 mmol) and 3-dimethylaminopropylamine (2.8 mg, 0.028 mmol) were added and the reaction was stirred at room temperature under nitrogen for one hour. The reaction mixture was then concentrated in vacuo to give a residue which was re-dissolved in 1:1 $H_2O:CH_3CN$ (5 mL). The resulting solution was purified by preparatory HPLC (conditions B). The desired fractions, as determined by analytical HPLC (conditions A) were concentrated in vacuo to ~1.5 mL, and desalted as in previous examples. After lyopholization 1,3-phenylenebis[oxy-1,3-n-propylene-oxy-4,1-phenylene) methylene]bis[A82846B,(3-dimethyl-aminopropyl)amide] (6.9 mg, 13.1% yield) and 1,3-phenylenebis[oxy-1,3-n-propylene-oxy-4,1-phenylene)-methylene]A82846B/A82846B,(3-dimethylaminopropyl)amide (6.6 mg, 12.8% yield) were obtained as white powders.

1,3-phenylenebis[oxy-1,3-n-propylene-oxy-4,1-phenylene)methylene]bis[A82846B,(3-dimethylaminopropyl)- amide]

HPLC (conditions A) retention time: 13.2 min.
FABMS shows peak of (M+9H) at 3761.

1,3-phenylenebis[oxy-1,3-n-propylene-oxy-4,1-phenylene)-methylene]A82846B/A82846B,(3-dimethylaminopropyl)amide HPLC (conditions A) retention time: 13.7 min.

FABMS shows peak of (M+6H) at 3674.

Details concerning the synthesis of all of the compounds of TABLES 1 and 2, as well as identifying characteristics on the same compounds, are presented in TABLES 3 and 4.

TABLE 3

| Ex. # | Aldehyde | HPLC* Retention Minutes | % yield | FAB · MS M/Z | M + xH |
|---|---|---|---|---|---|
| 1 | 1,2-bis(4-formylphenoxy)-n-ethane | 11.5 | 1.86 | 3136 | 3 |
| 2 | 1,4-bis(2-formylphenoxy)-n-butane | 11.8 | 0.79 | 3165 | 4 |
| 3 | 1,5-bis(4-formylphenoxy)-n-pentane | 12.9 | 5.42 | 3178 | 4 |
| 4 | 1,5-bis(3-formylphenoxy)-n-pentane | 13.0 | 4.08 | 3179 | 4 |
| 5 | 1,6-bis(4-formylphenoxy)-n-hexane | 13.6 | 9.05 | 3195 | 6 |
| 6 | 3-methyl-1,5-bis(4-formylphenoxy)-n-pentane | 13.5 | 4.54 | 3193 | 4 |
| 7 | 1,7-bis(4-formylphenoxy)-n-heptane | 14.7 | 5.00 | 3207 | 5 |
| 8 | 1,8-bis(4-formylphenoxy)-n-octane | 15.5 | 3.91 | 3219 | 2 |
| 9 | 1,9-bis(4-formylphenoxy)-n-nonane | 16.4 | 4.41 | 3235 | 4 |
| 10 | 1,2-bis(2-(4-formylphenoxy)-ethoxy)ethane | 12.3 | 1.89 | 3226 | 4 |
| 11 | 1,4-bis(2-(p-formylphenoxy)-ethoxy)carbonyl-benzene | 13.0 | 10.50 | 3331 | 6 |
| 12 | 1,3-bis(3-(p-formylphenoxy)-n-propyloxy)-benzene | 15.5 | 3.10 | 3300 | 4 |
| 13 | 1,8-bis(4-formylphenoxy)-n-octane | 14.5 | 5.95 | 3364 | 4 |
| 14 | 1,3-bis(4-formylphenoxy)-propane | 9.4 | 14.29 | 3436 | 4 |
| 15 | 1,4-bis(2-formylphenoxy)-n-butane | 10.2 | 5.91 | 3452 | 5 |
| 16 | 1,5-bis(4-formylphenoxy)-n-pentane | 10.4 | 3.86 | 3466 | 5 |
| 17 | 1,5-bis(3-formylphenoxy)-n-pentane | 11.3 | 22.41 | 3465 | 4 |
| 18 | 1,6-bis(4-formylphenoxy)-n-hexane | 11.3 | 5.46 | 3478 | 4 |
| 19 | 3-methyl-1,5-bis(4-formylphenoxy)-n-pentane | 11.3 | 8.14 | 3479 | 4 |
| 20 | 1,7-bis(4-formylphenoxy)-n-heptane | 12.5 | 5.73 | 3494 | 5 |
| 21 | 1,8-bis(4-formylphenoxy)-n-octane | 14.0 | 13.31 | 3508 | 5 |
| 23 | 1,8-bis(3-formylphenoxy)-n-octane | 14.4 | 21.23 | 3508 | 5 |
| 24 | 1,8-bis(4-formyl-2-n-pentyloxy-phenoxy)-n-octane | 20.8 | 16.91 | 3680 | 5 |
| 25 | 1,9-bis(4-formylphenoxy)-n-nonane | 14.9 | 9.31 | 3522 | 5 |
| 26 | 1,10-bis(4-formylphenoxy)-n-decane | 15.9 | 8.87 | 3535 | 5 |
| 27 | 1,12-bis(4-formylphenoxy)-n-dodecane | 17.7 | 1.32 | 3565 | 6 |
| 28 | 1,16-bis(4-formylphenoxy)-n-hexadecane | 20.4 | 4.05 | 3625 | 9 |
| 29 | 1,2-bis(2-(4-formylphenoxy)ethoxy)ethane | 10.2 | 6.28 | 3511 | 4 |
| 30 | 1,3-bis(3-(p-formylphenoxy)-n-propyloxy)-benzene | 15.2 | 22.96 | 3589 | 5 |
| 31 | 1,4-bis(2-(p-formylphenoxy)-ethoxy)carbonyl-benzene | 11.7 | 24.94 | 3615 | 5 |
| 32 | 5-phenyl-1,3-bis(3-(p-formylphenoxy)-n-propyloxy)-benzene | 16.8 | 12.88 | 3664 | 5 |
| 49 | 1,6-bis(4-(4-formylphenyl)-phenoxy) hexane | 16.2 | 11.58 | 3633 | 5 |
| 50 | 1,3-bis(5-(4-formylphenoxy)-n-pentyloxy)-benzene | 17.0 | 9.31 | 3645 | 6 |
| 51 | 1,8-bis(2-phenyl-5-formylphenoxy)-octane | 18.3 | 10.83 | 3662 | 6 |
| 53 | 1,8-bis(3-formylphenoxy)-n-hexane | 15.3 | 2.1 | 3221 | 4 |
| 54 | 1,6-bis(4-(4'-formylphenoxy)-phenoxy)-n-hexane | 18.2 | 6.1 | 3347 | 6 |
| 55 | 1,8-bis(3-formyl-2-iodophenoxy)-n-hexane | 22.9 | 2.2 | 3471 | 3 |
| 56 | 1,8-bis(2-phenyl-5-formylphenoxy)-n-octane | 19.3 | 2.8 | 3374 | 4 |
| 57 | 1,3-bis(6-(2-dimethyl)-1-hexanaloxy)-benzene | 15.5 | 8.2 | 3229 | 4 |
| 58 | 1,4-bis(6-(2-dimethyl)-1-hexanaloxy)-butane | 13.5 | 6.1 | 3209 | 4 |
| 59 | 1,12-bis(4-formylphenoxy)-n-dodecane | 21.6 | 6.8 | 3278 | 5 |
| 60 | 1,3-bis(3-(p-formylphenoxy-n-propyloxy)-benzene | HCL SALT | | | |
| 61 | 1,3-bis(3-(p- | 36.6 | 12.7 | 3660 | 8 |

TABLE 3-continued

| Ex. # | Aldehyde | HPLC* Retention Minutes | % yield | FAB · MS M/Z | M + xH |
|---|---|---|---|---|---|
| | formylphenoxy-n-propyloxy)-5-n-pentylbenzene | | | | |
| 62 | 1,8-bis(3-formyl-2-iodophenoxy)-n-octane | 17.1 | 5.4 | 3762 | 6 |
| 63 | 1,3-bis(6-(2-dimethyl)-1-hexanaloxy)-benzene | 13.3 | 15.5 | 3516 | 5 |
| 64 | 1,3-bis(3-(p-formylphenoxy-n-heptyloxy)-benzene | 19.3 | 1.4 | 3701 | 6 |
| 65 | 1,4-bis(6-(2-dimethyl)-1-hexanaloxy)-butane | 13.5 | 24.8 | 3495 | 4 |
| 66 | 1,3-bis(3-(p-formylphenoxy-n-propyloxy)-benzene | HCL SALT | | | |
| 70 | 1,3-bis(3-(p-formylphenoxy)n-propyloxy)-benzene | 13.7 | 12.8 | 3674 | 6 |
| 71 | 1,3-bis(3-(p-formylphenoxy)-n-propyloxy)-benzene | 13.2 | 13.1 | 3761 | 9 |

*Conditions A

TABLE 4

| Ex. # | Aldehyde | HPLC* Retention, Minutes | % Yield | FAB · MS M/Z | M + xH |
|---|---|---|---|---|---|
| 33 | 1,2-bis(4-formylphenoxy)-n-ethane | 13.1 | 2.58 | 1706 | 5 |
| 34 | 1,2-bis(4-formylphenoxy)-n-propane | 15.2 | 13.08 | 1718 | 0 |
| 35 | 1,2-bis(4-formylphenoxy)-n-butane | 14.7 | 8.12 | 1734 | 4 |
| 36 | 1,2-bis(4-formylphenoxy)-n-pentane | 17.1 | 21.89 | 1746 | 4 |
| 37 | 1,2-bis(4-formylphenoxy)-n-hexane | 18.0 | 8.37 | 1760 | 2 |
| 38 | 1,2-bis(4-formylphenoxy)-n-methyl-n-pentane | 17.7 | 5.81 | 1760 | 1 |
| 39 | 1,2-bis(4-formylphenoxy)-n-heptane | 19.0 | 27.99 | 1774 | 2 |
| 40 | 1,2-bis(4-formylphenoxy)-n-octane | 18.5 | 11.89 | 1789 | 3 |
| 41 | 1,2-bis(4-formylphenoxy)-n-decane | 21.7 | 0.85 | 1816 | 4 |
| 42 | 1,2-bis(4-formylphenoxy)-n-dodecane | 23.4 | 12.53 | 1841 | 1 |
| 43 | 1,2-bis(2-(4-formylphenoxy)ethoxyethane | 14.4 | 5.57 | 1794 | 4 |
| 44 | 1,2-bis(2-(4-formylphenoxy)ethoxy-benzoate | 16.5 | 5.64 | 1897 | 3 |
| 45 | 1,2-bis(2-(4-formylphenoxy)-propyloxy)-5-phenylbenzene | 21.0 | 4.96 | 1946 | 5 |
| 46 | 1,3-bis(4-formylphenoxy)-propane | 15.2 | 4.90 | 1861 | 2 |
| 47 | 1,3-bis(4-formylphenoxy)-octane | 19.9 | 8.69 | 1930 | 1 |
| 48 | 1,3-bis(4-formylphenoxy)-dodecane | 23.3 | 1.19 | 1984 | 1 |
| 52 | 1,3-bis(3-(p-formylphenoxy)-n-propyloxy)-benzene | 18.8 | 3.10 | 1871 | 5 |
| 67 | 1,8-bis(3-formyl-2-iodophenoxy)-n-octane | 21.3 | 4.5 | 2042 | 5 |
| 68 | 1,3-bis(6-(2-dimethyl)-1-hexanaloxy)-benzene | 18.3 | 13.2 | 1798 | 4 |
| 69 | 1,3-bis(3-(p-formylphenoxy-n-propyloxy)-5-n-pentylbenzene | 22.4 | 3 | 1940 | 5 |

*Conditions A

The compounds of Formulae I and II are useful for the treatment of bacterial infections. Therefore, in another embodiment, the present invention is directed to a method for controlling a bacterial infection in a host animal, typically a warm-blooded animal, which comprises administering to the host animal an effective, antibacterial amount of a compound of Formula I or II. In this embodiment, the compounds of the present invention can be used to control and treat infections due to various bacteria, but especially gram-positive bacteria. In a preferred embodiment, the compounds are used to control and treat infections due to bacteria resistant to existing antibacterials. For example, certain bacteria are resistant to methicillin, and yet others are resistant to vancomycin and/or teicoplanin. The present compounds provide a technique for controlling and treating infections due to such resistant bacterial species.

In carrying out this embodiment of the invention, the compounds can be administered by any of the conventional techniques, including the oral route and parenteral routes such as intravenous and intramuscular. The amount of compound to be employed is not critical and will vary depending on the particular compound employed, the route of administration, the severity of the infection, the interval between dosings, and other factors known to those skilled in the art. In general, a dose of from about 0.5 to about 100 mg/kg will be effective; and in many situations, lesser doses of from about 0.5 to about 50 mg/kg will be effective. A compound of the present invention can be administered in a single dose, but in the known manner of antibacterial therapy, a compound of the present invention is typically administered repeatedly over a period of time, such as a matter of days or weeks, to ensure control of the bacterial infection.

Also in accordance with known antibacterial therapy, a compound of the present invention is typically formulated for convenient delivery of the requisite dose. Therefore, in another embodiment, the present invention is directed to a pharmaceutical formulation comprising a compound of either Formula I or II, in combination with a pharmaceutically-acceptable carrier. Such carriers are well known for both oral and parenteral routes of delivery. In general, a formulation will comprise a compound of the present invention in a concentration of from about 0.1 to about 90% by weight, and often from about 1.0 to about 3%.

The antibacterial efficacy of the present compounds is illustrated by following TABLES 5 and 6. The minimal inhibitory concentrations (MICs) were determined using a standard broth micro-dilution assay. TABLE 6 presents a comparison of the activity of illustrative compounds against representative vancomycin-resistant and vancomycin-sensitive enterococci (*Enterococcus faecium* and *Enterococcus faecalis*, mean geometric MIC (mcg/mL), as determined by the standard broth micro-dilution assay.

TABLE 5

In Vitro Antimicrobial Activity

MIC (mcg/ml)/Compound

| Organism | Vancomycin | A82846B | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| Staphylococcus aureus 446 | 0.5 | 0.25 | 4 | 16 | 8 | 8 | 4 | 4 | 2 | 8 | 1 | 8 | 16 | 8 | 8 | 4 | 4 | 8 |
| Staphylococcus aureus 489 | 0.125 | ≤0.06 | 0.5 | 0.5 | 0.5 | 2 | 0.5 | 0.25 | 0.5 | 4 | 1 | 4 | 4 | 2 | 2 | 1 | 0.25 | 2 |
| Staphylococcus aureus 447 | 0.5 | 0.25 | 16 | >64 | 32 | 32 | 16 | 8 | 8 | 32 | 4 | 16 | 64 | 8 | 16 | 16 | 64 | >64 |
| Staphylococcus aureus X400 | 0.5 | 0.125 | 1 | 1 | 2 | 2 | 1 | 1 | 1 | 4 | 4 | 4 | 8 | 2 | 4 | 2 | 0.5 | 2 |
| Staphylococcus aureus X778 | 0.5 | 0.125 | 1 | 4 | 2 | 4 | 1 | 1 | 1 | 4 | 1 | 1 | 16 | 2 | 2 | 1 | 0.5 | 2 |
| Staphylococcus aureus 491 | 1 | 0.25 | 0.5 | 0.5 | 0.25 | 2 | 0.25 | 0.5 | 0.5 | 2 | 0.5 | 1 | 0.25 | 2 | 1 | 0.25 | 0.125 | 0.5 |
| Staphylococcus aureus S13E | 0.5 | 0.125 | 2 | 2 | 2 | 4 | 1 | 2 | 1 | 8 | 2 | 4 | 8 | 4 | 4 | 4 | 1 | 1 |
| Staphylococcus aureus SA1199 | 0.5 | 0.125 | 4 | 4 | 32 | 4 | 2 | 4 | 1 | 16 | | 4 | 16 | 4 | | 4 | | 4 |
| Staphylococcus aureus SA1199A | 0.125 | ≤0.06 | 0.5 | 0.125 | 0.5 | 1 | 0.25 | 0.5 | 0.25 | 2 | 0.25 | 4 | 1 | 1 | 0.5 | 0.125 | ≤0.06 | 0.5 |
| Staphylococcus aureus SA119913 | 0.5 | 0.125 | 4 | 4 | 16 | 4 | 2 | 4 | 2 | 8 | 0.5 | 4 | 32 | 4 | 4 | 2 | 4 | 2 |
| Staphylococcus haemolyticus 105 | 16 | 1 | 8 | 4 | 8 | 8 | 4 | 8 | 2 | 8 | 0.5 | 4 | 64 | 4 | 1 | 4 | 1 | 1 |
| Staphylococcus haemolyticus 415 | 8 | 4 | 16 | >64 | 16 | 16 | 8 | 8 | 8 | 8 | 4 | 16 | 64 | 4 | 8 | 16 | >64 | 32 |
| Staphylococcus epidermidis 270 | 16 | 0.25 | 8 | >64 | 16 | 16 | 8 | 8 | 4 | 8 | 2 | 16 | 32 | 4 | 8 | 8 | 64 | 32 |
| Enterococcus faecium 180 | >64 | 8 | 0.25 | 1 | 1 | ≤0.06 | ≤0.06 | ≤0.06 | ≤0.06 | 0.125 | ≤0.06 | 4 | 2 | 4 | 0.125 | 0.25 | 0.25 | 0.125 |
| Enterococcus faecium 180-1 | 0.5 | 0.125 | 0.5 | 1 | 0.5 | 1 | 0.25 | ≤0.06 | ≤0.06 | 0.5 | 0.25 | 1 | 0.25 | 0.25 | 0.5 | ≤0.06 | 0.25 | 0.5 |
| Enterococcus faecalis 2041 | 2 | 0.25 | 0.25 | 0.25 | ≤0.06 | ≤0.06 | ≤0.06 | ≤0.06 | 0.5 | 0.25 | 0.5 | 0.25 | 0.5 | 1 | 0.25 | 0.25 | 0.125 | 0.25 |
| Enterococcus faecalis 276 | 1 | 0.125 | 0.25 | 0.66 | 0.5 | 0.25 | 0.5 | 0.5 | 1 | 2 | 1 | 0.125 | 0.5 | | 1 | 0.5 | 0.5 | 1 |
| Enterococcus gallinarum 245 | 4 | 0.25 | 0.06 | 0.06 | 0.06 | 0.06 | 0.06 | 0.06 | 0.06 | 0.25 | 0.06 | 0.125 | 0.06 | 0.06 | 0.06 | 0.06 | 0.06 | 0.25 |
| Haemophilus influenzae RD | >64 | >64 | >64 | >64 | >64 | >64 | >64 | >64 | >64 | >64 | >64 | 64 | >64 | >64 | >64 | >64 | >64 | >64 |
| Escherichia coli EC14 | >64 | >64 | >64 | >64 | >64 | >64 | >64 | >64 | >64 | >64 | >64 | >64 | >64 | >64 | >64 | >64 | >64 | >64 |
| Streptococcus pyogenes C203 | 0.5 | | 0.06 | 0.06 | 0.06 | 0.06 | 0.06 | 0.06 | 0.06 | 8 | 0.06 | 0.06 | 0.06 | 0.06 | 0.06 | 0.06 | 0.06 | 1 |
| Streptococcus pneumoniae P1 | 0.25 | | 0.06 | 0.06 | 0.06 | | 0.06 | 0.06 | 0.06 | 4 | 0.06 | 0.06 | 0.06 | 0.06 | 0.06 | 0.06 | 0.125 | 1 |

MIC (mcg/ml)/Compound

| Organism | 17 | 18 | 19 | 20 | 21 | 22 | 23 | 24 | 25 | 26 | 27 | 28 | 29 | 30 | 31 | 32 | 33 | 34 |
|---|---|---|---|---|---|---|---|---|---|---|---|---|---|---|---|---|---|---|
| Staphylococcus aureus 446 | 4 | 8 | 4 | 4 | 8 | 4 | 2 | 2 | 4 | 4 | 16 | >64 | 16 | 1 | 1 | 16 | 0.25 | ≤0.06 |
| Staphylococcus aureus 489 | 1 | 4 | 0.25 | 2 | 2 | 4 | 1 | 2 | 4 | 2 | 8 | 64 | 1 | 1 | 1 | 4 | ≤0.06 | ≤0.06 |
| Staphylococcus aureus 447 | >64 | 64 | 32 | 64 | 64 | 32 | 8 | 16 | 64 | >64 | >64 | >64 | 64 | 4 | 8 | >64 | 0.5 | ≤0.06 |
| Staphylococcus aureus X400 | 2 | 2 | 0.5 | 2 | 2 | 4 | 4 | 2 | 2 | 2 | 16 | 32 | 2 | 1 | 0.5 | 4 | ≤0.06 | ≤0.06 |
| Staphylococcus aureus X778 | 2 | 2 | 2 | 1 | 1 | 1 | 0.25 | 1 | 1 | 1 | 2 | 32 | 2 | 0.5 | 0.25 | 2 | 0.125 | ≤0.06 |
| Staphylococcus aureus 491 | 0.5 | 0.25 | 0.25 | 2 | 2 | 2 | 4 | 2 | 2 | 2 | 8 | 16 | ≤0.06 | 0.25 | ≤0.06 | 2 | ≤0.06 | ≤0.06 |
| Staphylococcus aureus S13E | 1 | 2 | 1 | 2 | 1 | 2 | 2 | 2 | 4 | 2 | 8 | 64 | 4 | 0.5 | 0.25 | 8 | 0.125 | ≤0.06 |
| Staphylococcus aureus SA1199 | 1 | 2 | | 4 | | | | | | | 8 | 64 | 2 | 1 | 0.5 | 8 | 0.25 | ≤0.06 |

TABLE 5-continued

In Vitro Antimicrobial Activity

| Organism | 35 | 36 | 37 | 38 | 39 | 40 | 41 | 42 | 43 | 44 | 45 | 46 | 47 | 48 | 49 | 50 | 51 |
|---|---|---|---|---|---|---|---|---|---|---|---|---|---|---|---|---|---|
| Staphylococcus aureus SA1199A | 0.125 | 0.25 | 0.125 | 0.25 | 0.25 | 0.5 | 0.5 | 1 | 0.5 | 1 | 1 | 16 | 0.5 | ≦0.06 | ≦0.06 | 2 | <0.06 |
| Staphylococcus aureus SA119913 | 1 | 1 | 2 | 2 | 1 | 4 | 1 | 2 | 2 | 2 | 2 | 64 | 4 | 1 | 0.5 | 8 | 0.125 |
| Staphylococcus haemolyticus 105 | 0.5 | 0.5 | 8 | 16 | 16 | 4 | 4 | 4 | 4 | 4 | 32 | 32 | 0.25 | 0.25 | 0.25 | 4 | 1 |
| Staphylococcus haemolyticus 415 | 8 | 16 | 32 | 32 | 8 | 16 | 4 | 4 | 16 | 16 | 64 | 64 | >64 | 4 | 16 | 8 | >64 |
| Staphylococcus epidermidis 270 | 64 | 16 | 16 | 16 | 8 | 8 | 4 | 4 | 16 | 8 | 32 | 64 | 32 | 4 | 4 | 8 | 4 |
| Enterococcus faecium 180 | 0.125 | ≦0.06 | 0.125 | ≦0.06 | 0.125 | 0.25 | 1 | 1 | 1 | 1 | 1 | 8 | 0.25 | 0.125 | 2 | 16 | 0.5 |
| Enterococcus faecium 180-1 | 0.125 | 0.25 | 0.125 | 1 | 0.5 | 0.5 | 0.125 | 0.5 | 0.25 | ≦0.06 | 0.5 | 8 | 0.25 | 0.125 | 1 | 1 | 16 |
| Enterococcus faecalis 2041 | 0.125 | 0.25 | 0.25 | ≦0.06 | ≦0.06 | 0.5 | 0.5 | 1 | 1 | ≦0.06 | 0.5 | 8 | 0.5 | 0.125 | ≦0.06 | 2 | 0.125 |
| Enterococcus faecalis 276 | 0.125 | 0.125 | 1 | 0.25 | 0.5 | 0.5 | 1 | 1 | 1 | ≦0.06 | 0.5 | 8 | 0.125 | 0.25 | ≦0.06 | 2 | 0.25 |
| Enterococcus gallinarum 245 | 0.06 | 0.06 | 0.06 | 0.06 | 0.25 | 1 | 0.125 | 2 | 1 | ≦0.06 | 0.5 | 1 | 0.25 | 0.5 | 0.125 | 2 | 0.125 |
| Haemophilus influenzae RD | >64 | >64 | >64 | >64 | >64 | >64 | >64 | >64 | 0.25 | ≦0.06 | ≦0.06 | 0.125 | 0.06 | 0.125 | 0.06 | 1 | 2 |
| Escherichia coli EC14 | >64 | >64 | >64 | >64 | >64 | >64 | >64 | >64 | >64 | >64 | >64 | >64 | >64 | >64 | >64 | >64 | |
| Streptococcus pyogenes C203 | 0.06 | 0.06 | 0.06 | 0.06 | 0.06 | 0.06 | 0.25 | 0.25 | 0.06 | 0.06 | 0.06 | ≦0.06 | ≦0.06 | 0.06 | 0.06 | 0.5 | 0.06 |
| Streptococcus pneumoniae P1 | 0.06 | 0.06 | 0.06 | 0.06 | 0.06 | 0.06 | 0.25 | 1 | 0.06 | ≦0.06 | 0.06 | ≦0.06 | 0.06 | 0.06 | 0.06 | 0.125 | 1 |

MIC (mcg/ml)/Compound

| Organism | 35 | 36 | 37 | 38 | 39 | 40 | 41 | 42 | 43 | 44 | 45 | 46 | 47 | 48 | 49 | 50 | 51 | 53 |
|---|---|---|---|---|---|---|---|---|---|---|---|---|---|---|---|---|---|---|
| Staphylococcus aureus 446 | ≦0.06 | ≦0.06 | 0.25 | 0.125 | ≦0.06 | 0.5 | 4 | 2 | 2 | 0.125 | 1 | 1 | 8 | >64 | 16 | 2 | 16 | 8 |
| Staphylococcus aureus 489 | ≦0.06 | ≦0.06 | ≦0.06 | ≦0.06 | ≦0.06 | 0.125 | 2 | 2 | 1 | 0.125 | 2 | 0.5 | 4 | 32 | 4 | 2 | 8 | 2 |
| Staphylococcus haemolyticus 447 | ≦0.06 | 0.125 | ≦0.06 | ≦0.06 | 1 | 0.25 | 8 | 4 | 4 | 0.125 | 1 | 2 | 8 | >64 | >64 | 2 | >64 | 16 |
| Staphylococcus aureus X400 | ≦0.06 | ≦0.06 | ≦0.06 | ≦0.06 | 0.5 | 0.125 | 4 | 2 | 2 | ≦0.06 | 0.5 | 1 | 8 | 32 | 8 | 1 | 4 | 4 |
| Staphylococcus aureus X778 | ≦0.06 | ≦0.06 | ≦0.06 | 0.125 | 0.5 | ≦0.06 | 2 | 1 | 2 | ≦0.06 | 0.5 | 0.5 | 8 | 32 | 4 | 1 | 4 | 4 |
| Staphylococcus aureus 491 | ≦0.06 | ≦0.06 | ≦0.06 | ≦0.06 | ≦0.06 | ≦0.06 | 4 | 4 | 2 | ≦0.06 | 0.5 | 0.5 | 16 | 32 | 8 | 2 | 32 | 8 |
| Staphylococcus aureus S13E | ≦0.06 | ≦0.06 | ≦0.06 | ≦0.06 | 0.5 | 0.25 | 4 | 4 | 2 | ≦0.06 | 0.5 | 0.5 | 16 | 32 | 8 | 1 | 8 | 4 |
| Staphylococcus aureus SA1199 | ≦0.06 | ≦0.06 | ≦0.06 | ≦0.06 | 0.25 | ≦0.06 | 4 | 1 | 0.5 | ≦0.06 | 0.5 | 1 | 0.5 | 16 | 4 | 2 | 32 | 8 |
| Staphylococcus aureus SA119913 | ≦0.06 | ≦0.06 | ≦0.06 | ≦0.06 | ≦0.06 | ≦0.06 | 0.25 | 2 | 4 | ≦0.06 | ≦0.06 | 0.125 | 0.5 | 32 | 16 | 0.5 | 8 | 1 |
| Staphylococcus haemolyticus 105 | 0.25 | 0.25 | 0.5 | 0.5 | 0.125 | 1 | 8 | 4 | 4 | 0.25 | 0.5 | 2 | 8 | >64 | 4 | 2 | 2 | 16 |
| Staphylococcus haemolyticus 415 | 4 | 2 | 2 | 2 | 0.5 | 4 | 16 | 8 | 8 | 2 | 2 | 4 | 16 | >64 | 8 | 0.5 | 16 | 2 |
| Staphylococcus epidermidis 270 | ≦0.06 | ≦0.06 | ≦0.06 | ≦0.06 | 0.25 | 0.25 | 4 | 4 | 4 | 0.25 | 2 | 2 | 4 | >64 | 8 | 2 | 8 | 8 |
| Enterococcus faecium 180 | 2 | 0.25 | 0.5 | 0.5 | 1 | 1 | 16 | 0.5 | 8 | 4 | 1 | 0.5 | 0.5 | 64 | 1 | 1 | 1 | 4 |
| Enterococcus faecium 180-1 | 0.125 | ≦0.06 | ≦0.06 | ≦0.06 | ≦0.06 | ≦0.06 | 2 | 1 | 0.5 | ≦0.06 | 0.5 | ≦0.06 | 1 | 8 | 2 | 0.5 | 1 | <.06 |
| Enterococcus faecalis 2041 | 0.125 | ≦0.06 | ≦0.06 | ≦0.06 | ≦0.06 | 0.125 | 4 | 2 | 1 | ≦0.06 | 0.5 | ≦0.06 | 2 | 8 | 2 | 0.25 | 2 | 0.25 |
| Enterococcus faecalis 276 | ≦0.06 | ≦0.06 | 0.25 | 0.25 | ≦0.06 | 0.25 | 4 | 4 | 1 | ≦0.06 | 0.25 | 4 | 8 | 32 | 0.5 | 0.125 | 4 | 0.5 |
| Enterococcus gallinarum 245 | 1 | 0.25 | 1 | 0.5 | 0.25 | 1 | 8 | 1 | 0.5 | 0.25 | 0.5 | 4 | 16 | >64 | 0.5 | 0.5 | 1 | 0.25 |
| Haemophilus influenzae RD | >64 | >64 | >64 | >64 | >64 | >64 | >64 | >64 | >64 | >64 | >64 | >64 | >64 | >64 | >64 | >64 | >64 | >64 |
| Escherichia coli EC14 | 0.06 | 0.06 | 0.06 | 0.06 | 0.06 | 0.06 | 0.25 | 0.25 | 0.06 | 0.06 | 0.06 | ≦0.06 | ≦0.06 | 2 | 2 | ≦0.06 | >64 | >64 |
| Streptococcus pyogenes C203 | 0.06 | 0.06 | 0.06 | 0.06 | 0.06 | 0.06 | 0.25 | 1 | 0.06 | 0.06 | 0.06 | ≦0.06 | ≦0.06 | 4 | 2 | >64 | 1 | 0.06 |
| Streptococcus pneumoniae P1 | | | | | | | | | | | | | | | | 0.125 | 1 | 0.06 |

TABLE 5-continued

In Vitro Antimicrobial Activity

MIC (mcg/ml)/Compound

| Organism | 54 | 55 | 56 | 57 | 58 | 59 | 60 | 61 | 62 | 63 | 64 | 65 | 66 | 67 | 68 | 69 | 70 | 71 |
|---|---|---|---|---|---|---|---|---|---|---|---|---|---|---|---|---|---|---|
| Staphylococcus aureus 446 | 8 | 8 | >64 | 8 | 32 | 64 | 8 | 8 | 8 | 4 | 16 | 8 | 0.5 | 2 | 1 | 32 | 2 | 4 |
| Staphylococcus aureus 489 | 2 | 2 | >64 | 2 | 1 | 32 | 1 | 4 | 2 | 1 | 8 | 0.5 | 0.25 | 1 | 0.25 | 32 | 0.5 | 2 |
| Staphylococcus aureus 447 | 16 | 32 | >64 | 32 | >64 | >64 | 8 | 16 | 32 | 64 | >64 | 32 | 1 | 4 | 0.25 | 64 | 2 | 4 |
| Staphylococcus aureus X400 | 2 | 4 | >64 | 4 | 4 | 32 | 2 | 8 | 2 | 1 | 16 | 1 | 0.5 | 1 | 0.125 | 16 | 1 | 4 |
| Staphylococcus aureus X778 | 2 | 4 | >64 | 4 | 8 | 16 | 2 | 4 | 2 | 1 | 8 | 1 | 0.5 | 2 | 0.125 | 32 | 1 | 2 |
| Staphylococcus aureus 491 | 1 | 2 | >64 | 1 | 1 | 8 | 1 | 2 | 2 | 0.5 | 8 | 0.5 | <.06 | 4 | 0.25 | 16 | 0.5 | 2 |
| Staphylococcus aureus S13E | 4 | 4 | >64 | 8 | 8 | >64 | 2 | 16 | 4 | 1 | 32 | 4 | 1 | 4 | 0.5 | 16 | 1 | 4 |
| Staphylococcus aureus SA1199 | 4 | 4 | >64 | 4 | 16 | 32 | 2 | 8 | 2 | 1 | 16 | 4 | 1 | 4 | 0.25 | 32 | 1 | 2 |
| Staphylococcus aureus SA1199A | 2 | 2 | >64 | 1 | 8 | 16 | 0.5 | 1 | 1 | 0.125 | 4 | 0.5 | 0.5 | 0.5 | <0.6 | 4 | 0.25 | 2 |
| Staphylococcus aureus SA119913 | 2 | 4 | >64 | 4 | 8 | 32 | 2 | 16 | 2 | 1 | 16 | 2 | 1 | 2 | 0.25 | 32 | 1 | 2 |
| Staphylococcus haemolyticus 105 | 8 | 2 | >64 | 2 | 2 | 16 | 8 | 1 | 4 | 1 | 8 | 4 | 1 | 2 | 0.5 | 4 | 0.5 | 2 |
| Staphylococcus haemolyticus 415 | 16 | 16 | >64 | 32 | >64 | 64 | 8 | 8 | 4 | 32 | 8 | 32 | 2 | 2 | 4 | 64 | 1 | 2 |
| Staphylococcus epidermidis 270 | 8 | 8 | >64 | 8 | 32 | 32 | 4 | 4 | 2 | 1 | 8 | 4 | 0.5 | 1 | 0.25 | 4 | 1 | 1 |
| Enterococcus faecium 180 | 1 | 2 | 8 | 0.25 | 2 | 2 | 0.125 | 1 | 1 | 0.5 | 2 | 1 | 0.25 | 1 | 1 | 2 | 1 | 2 |
| Enterococcus faecium 180-1 | 1 | 1 | 8 | 0.5 | 1 | 4 | 1 | 0.5 | 1 | <.06 | 0.5 | 0.25 | <.06 | 0.5 | <.06 | 2 | 0.25 | 0.5 |
| Enterococcus faecalis 2041 | 2 | 2 | 16 | <.06 | 0.25 | 4 | 0.25 | 2 | 1 | <.06 | 2 | 0.25 | <.06 | 0.5 | 0.125 | 1 | 0.5 | 0.5 |
| Enterococcus faecalis 276 | 1 | 4 | 32 | 0.5 | 0.5 | 8 | 0.25 | 2 | 1 | 0.5 | 2 | 0.125 | 0.25 | 2 | 0.125 | 8 | 0.5 | 1 |
| Enterococcus gallinarum 245 | 1 | 4 | 8 | 0.06 | 1 | 1 | 0.06 | 1 | 1 | 0.06 | 2 | 0.06 | 0.06 | 2 | 1 | 2 | 0.5 | 0.5 |
| Haemophilus influenzae RD | >64 | 4 | >64 | >64 | >64 | >64 | >64 | >64 | >64 | >64 | >64 | >64 | >64 | >64 | >64 | >64 |  |  |
| Escherichia coli EC14 | >64 | >64 | >64 | >64 | >64 | >64 | 2 | >64 | >64 | >64 | 2 | 1 | >64 | 4 | 0.06 | 0.25 | 0.125 | 0.5 |
| Streptococcus pyogenes C203 | 1 | 16 | 8 | 0.06 | 0.06 | 1 | 0.06 | 1 | 8 | 0.06 | 2 | 0.06 | 0.06 | 4 | 0.06 | 1 | 0.06 | 0.5 |
| Streptococcus pneumoniae P1 | 1 | 8 | 16 | 0.06 | 0.06 | 2 | 0.06 | 2 | 4 | 0.06 | 1 | 0.06 | 0.06 | 4 | 0.06 |  |  |  |

TABLE 6

In Vitro Activity Against Enterococci

| Cpd. Number | Vancomycin Resistant Strains | Vancomycin Sensitive Strains |
| --- | --- | --- |
| Vancomycin | 282 | 3.9 |
| A82846B | 29 | 0.22 |
| 1 | 42 | 1.3 |
| 2 | 27 | 1.0 |
| 3 | 27 | 1.5 |
| 4 | 19 | 2.0 |
| 5 | 11 | 0.87 |
| 6 | 32 | 1.3 |
| 7 | 8.0 | 1.3 |
| 8 | 9.5 | 0.87 |
| 9 | 9.5 | 1.2 |
| 10 | >90 | 3.0 |
| 11 | 38 | 1.7 |
| 12 | 4.0 | 0.66 |
| 13 | 9.5 | 1.2 |
| 14 | >64 | 1.0 |
| 15 | 23 | 0.87 |
| 16 | 38 | 1.5 |
| 17 | 4.8 | 0.57 |
| 18 | 19 | 1.0 |
| 19 | 19 | 0.76 |
| 20 | 13 | 1.0 |
| 21 | 2.8 | 0.87 |
| 22 | 6.7 | 0.76 |
| 23 | 1.7 | 0.5 |
| 24 | 4.8 | 1.2 |
| 25 | 6.7 | 1.2 |
| 26 | 4.0 | 1.5 |
| 27 | 3.4 | 1.7 |
| 28 | 9.5 | 6.1 |
| 29 | 38 | 1.3 |
| 30 | 1.7 | 0.38 |
| 31 | 27 | 0.66 |
| 32 | 2.8 | 1.5 |
| 33 | >128 | 1.3 |
| 34 | 53 | 0.87 |
| 35 | >81 | 0.57 |
| 36 | 6.7 | 0.29 |
| 37 | 9.5 | 9.1 |
| 38 | 4.8 | 1.1 |
| 39 | 5.7 | 1.0 |
| 40 | 11.3 | 0.19 |
| 41 | 3.4 | 1.1 |
| 42 | 4.5 | 1.1 |
| 43 | >128 | 4.6 |
| 44 | 76 | 0.66 |
| 45 | 2.8 | 0.33 |
| 46 | 4.8 | 0.17 |
| 47 | 2.8 | 1.0 |
| 48 | 8.0 | 5.2 |
| 49 | 2.0 | 1.5 |
| 50 | 1.7 | 0.44 |
| 51 | 3.4 | 2.3 |
| 52 | 4.8 | 0.093 |
| 53 | 5.7 | 0.66 |
| 54 | 4.8 | 2.3 |
| 55 | 4.8 | 2.3 |
| 56 | 8 | 5.3 |
| 57 | 11.3 | 0.76 |
| 58 | 64 | 1 |
| 59 | 2.4 | 1.2 |
| 60 | 2.4 | 1.3 |
| 61 | 2 | 1.2 |
| 62 | 3.4 | 1.5 |
| 63 | 4.8 | 0.57 |
| 64 | 6.7 | 4 |
| 65 | 22 | 0.57 |
| 66 | 2 | 0.38 |
| 67 | 3.4 | 0.66 |
| 68 | 9.5 | 0.25 |
| 69 | 5.7 | 2.3 |
| 70 | 3.4 | 0.38 |
| 71 | 2.4 | 0.38 |

We claim:

1. A compound of the formula:

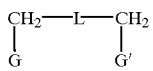

wherein each of G and G' is independently deshydrovancomycin of the formula:

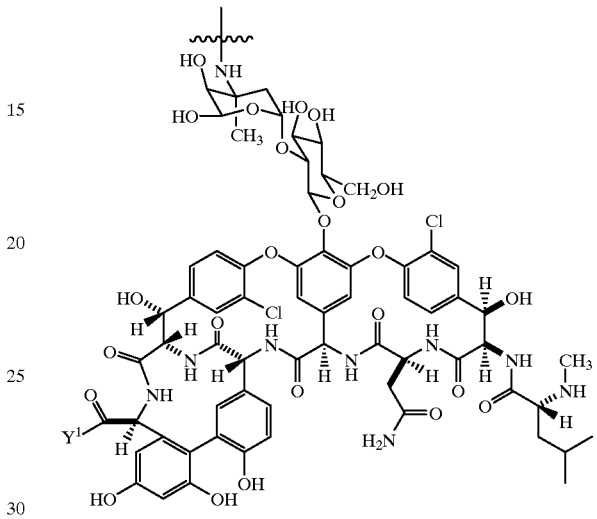

or deshydroA82846B of the formula:

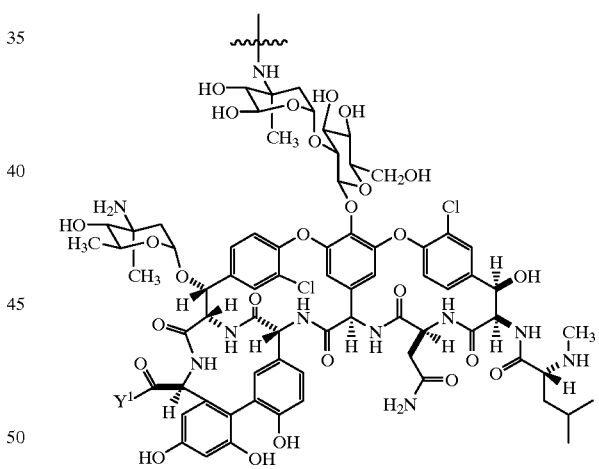

wherein $Y^1$ is OH or

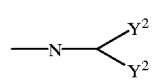

and $Y^2$ is defined as follows:

(1) each $Y^2$ independently represents
hydrogen,
alkyl of $C_1$–$C_{10}$,
cycloalkyl of $C_5$–$C_6$,
cycloalkenyl of $C_5$–$C_6$,
naphthyl,
biphenylyl, a radical of the formula —$Y^3$—$(Y^4)_{0, 1, \text{or } 2}$, wherein $Y^3$ is loweralkyl of $C_1$–$C_6$ optionally substituted by from one to three substituents, each of which is independently selected from the group consisting of halo, nitro, cyano, alkoxy, haloalkyl, and haloalkoxy; and $Y^4$ is

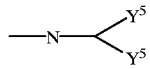

wherein each $Y^5$ is independently hydrogen or loweralkyl of $C_1$–$C_4$, or $Y^4$ is phenyl or phenyl substituted with from one to three substituents, each of which is independently
   halo,
   nitro,
   loweralkyl of $C_1$–$C_4$,
   cycloalkyl of $C_5$–$C_6$,
   loweralkoxy of $C_1$–$C_4$,
   haloloweralkyl of $C_1$–$C_4$, or
   haloloweralkoxy of $C_1$–$C_4$; or
(2) one $Y^2$ is hydrogen and the other $Y^2$ is (2-furanon-3-yl); or
(3) both $Y^2$ moieties are taken together with the nitrogen and constitute a five- to seven-membered heterocyclic ring optionally containing in addition to the indicated nitrogen atom one additional hetero ring atom which is nitrogen, oxygen, or sulfur, and which heterocyclic radical can be unsubstituted or substituted with from one or two substituents, each of which is loweralkyl of $C_1$–$C_2$, loweralkoxy of $C_1$–$C_2$, phenyl, benzyl, or $C_1$–$C_6$-alkanoyl; and L is a divalent linking radical of the formula Ia:

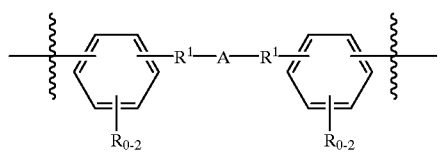

Ia wherein A is:
   alkylene of $C_1$–$C_{16}$,
   $(Z^1$—$X')_q$—$Z^1$,

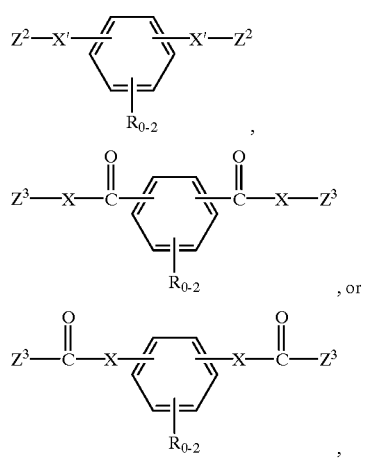

where q is 1–3, each $Z^1$ is independently an alkylene of $C_1$–$C_4$, each $Z^2$ is independently an alkylene of $C_1$–$C_8$, each $Z^3$ is independently an alkylene of $C_1$–$C_2$, each X is independently —O— or

where $R^2$ is H or loweralkyl of $C_1$–$C_4$; and each X' is independently —O—, —S—, or

where $R^2$ is as defined above, and each R independently represents halo, loweralkyl of $C_1$–$C_6$, loweralkoxy of $C_1$–$C_6$, phenyl, or phenyl substituted by from 1 to 2 substituents, each of which is independently halo, loweralkyl of $C_1$–$C_6$, or loweralkoxy of $C_1$–$C_6$,
each $R^1$ is independently
   $CH_2$,
   O,
   S,

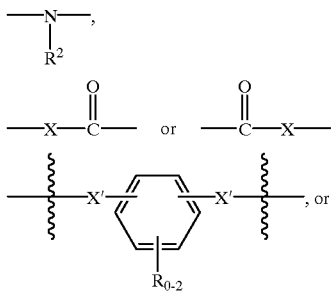

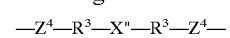

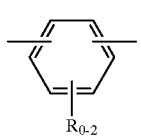

wherein R, X, X' and $R^2$ are as defined above; or L is a divalent linking radical of the formula Ib:

$$-Z^4-R^3-X''-R^3-Z^4-$$  Ib wherein each $Z^4$ is independently an alkylene of $C_1$–$C_8$; X" represents alkylene of $C_1$–$C_4$ or a phenylene of the formula wherein R is as defined above; and each $R^3$ is independently $CH_2$ or O; or a salt thereof.

2. A compound of claim 1 wherein both of G and G' are deshydro A82846B.

3. A compound of claim 1 or 2 wherein L is a linking radical of formula A, A is alkylene of $C_1$–$C_{16}$, and both $R^1$ are O.

4. A compound of claim 3 wherein A is straight-chain alkylene of $C_6$–$C_{12}$.

5. A compound of claim 1 or 2 wherein L is a linking radical of formula A, A is (alkylene of $C_1$–$C_4$—X')$_q$-alkylene of $C_1$–$C_4$, q=2, and both $R^1$ are O.

6. A compound of the formula:

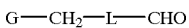

wherein G is selected from the group consisting of deshydrovancomycin of the formula:

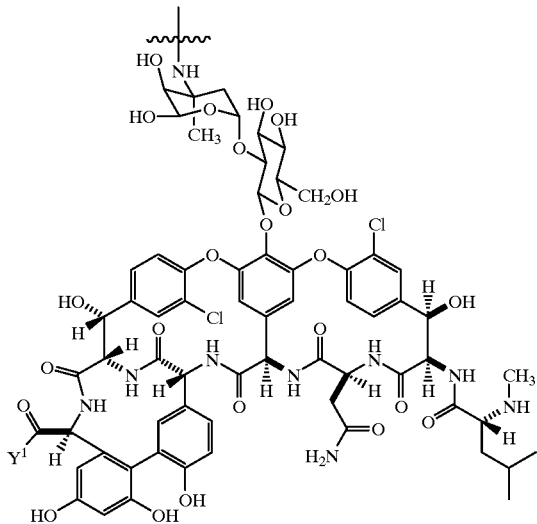

and deshydroA82846B of the formula:

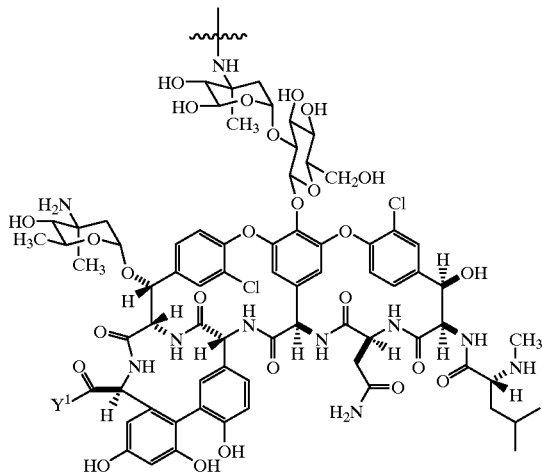

wherein $Y^1$ is OH or

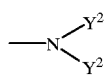

and $Y^2$ is defined as follows:
(1) each $Y^2$ independently represents
hydrogen,
alkyl of $C_1$–$C_{10}$,
cycloalkyl of $C_5$–$C_6$,
cycloalkenyl of $C_5$–$C_6$,
naphthyl,
biphenylyl,
a radical of the formula —$Y^3$—($Y^4$)$_{0, 1, or 2}$, wherein $Y^3$ is loweralkyl of $C_1$–$C_6$ optionally substituted by from one to three substituents, each of which is independently selected from the group consisting of halo, nitro, cyano, alkoxy, haloalkyl, and haloalkoxy; and $Y^4$ is

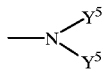

wherein each $Y^5$ is independently hydrogen or loweralkyl of $C_1$–$C_4$, or $Y^4$ is phenyl or phenyl substituted with from one to three substituents, each of which is independently
halo,
nitro,
loweralkyl of $C_1$–$C_4$,
cycloalkyl of $C_5$–$C_6$,
loweralkoxy of $C_1$–$C_4$,
haloloweralkyl of $C_1$–$C_4$, or
haloloweralkoxy of $C_1$–$C_4$; or (2) one $Y^2$ is hydrogen and the other $Y^2$ is (2-furanon-3-yl); or (3) both $Y^2$ moieties are taken together with the nitrogen and constitute a five- to seven-membered heterocyclic ring optionally containing in addition to the indicated nitrogen atom one additional hetero ring atom which is nitrogen, oxygen, or sulfur, and which heterocyclic radical can be unsubstituted or substituted with from one or two substituents, each of which is loweralkyl of $C_1$–$C_2$, loweralkoxy of $C_1$–$C_2$, phenyl, benzyl, or $C_1$–$C_6$-alkanoyl; and L is a divalent linking radical of the formula Ia:

Ia

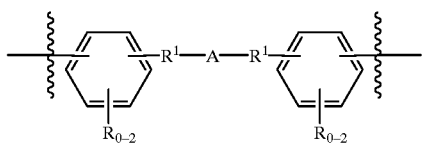

wherein A is:
alkylene of $C_1$–$C_{16}$,
($Z^1$—$X'$)$_q$-$Z^1$,

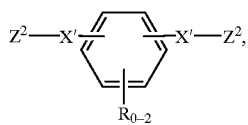

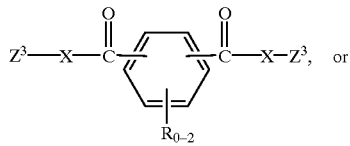

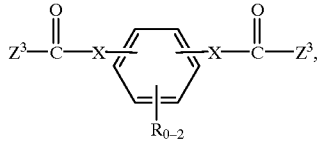

where q is 1–3, each $Z^1$ is independently an alkylene of $C_1$–$C_4$, each $Z^2$ is independently an alkylene of $C_1$–$C_8$, each $Z^3$ is independently an alkylene of $C_1$–$C_2$, each X is independently —O— or

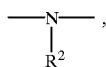

where $R^2$ is H or loweralkyl of $C_1$–$C_4$; and each X' is independently —O—, —S—, or

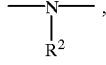

where $R^2$ is as defined above, and each R independently represents halo, loweralkyl of $C_1$–$C_6$, loweralkoxy of $C_1$–$C_6$, phenyl, or phenyl substituted by from 1 to 2 substituents, each of which is independently halo, loweralkyl of $C_1$–$C_6$, or loweralkoxy of $C_1$–$C_6$, each $R^1$ is independently $CH_2$,
O,
S,

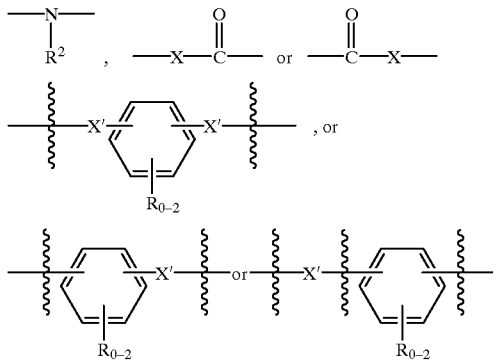

wherein R, X, X' and $R^2$ are as defined above; or L is a divalent linking radical of the formula Ib:

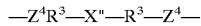   Ib wherein each $Z^4$ is independently an alkylene of $C_1$–$C_8$; X" represents alkylene of $C_1$–$C_4$ or a phenylene of the formula

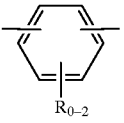

wherein R is as defined above; and each $R^3$ is independently $CH_2$ or O; or a salt thereof.

7. A pharmaceutical formulation comprising a compound of claim 1 or 6 in combination with a pharmaceutically-acceptable diluent or carrier.

8. A method of treating a bacterial infection in a host comprising the step of administering to the host an effective amount of a compound of claim 1 or 6.

9. A method of claim 8 wherein the bacterial infection is attributable to a vancomycin-resistant-enterococcus.

10. A compound of claim 1 or 6 for use in antibacterial therapy.

11. A compound of claim 1 or 6 for use in antibacterial therapy against vancomycin-resistant-enterococcus.

12. A process for the preparation of a compound of claim 1 comprising the step of reducing a Schiff base corresponding to said compound of claim 1.

13. The process of claim 12 further comprising the step of forming a pharmaceutically acceptable salt of said compound.

14. A process for the preparation of a compound of claim 6 comprising the step of reducing a Schiff base corresponding to said compound of claim 6.

15. The process of claim 14 further comprising the step of forming a pharmaceutically acceptable salt of said compound.

* * * * *